(12) United States Patent
Yoneda et al.

(10) Patent No.: US 7,618,156 B2
(45) Date of Patent: Nov. 17, 2009

(54) LIGHT IRRADIATION DEVICE

(75) Inventors: Kenji Yoneda, Kyoto (JP); Kenji Miura, Kyoto (JP)

(73) Assignee: CCS Inc., Kyoto (JP)

( * ) Notice: Subject to any disclaimer, the term of this patent is extended or adjusted under 35 U.S.C. 154(b) by 108 days.

(21) Appl. No.: 11/720,420

(22) PCT Filed: Nov. 29, 2005

(86) PCT No.: PCT/JP2005/021898

§ 371 (c)(1),
(2), (4) Date: Apr. 9, 2008

(87) PCT Pub. No.: WO2006/059609

PCT Pub. Date: Jun. 8, 2006

(65) Prior Publication Data

US 2009/0002994 A1     Jan. 1, 2009

(30) Foreign Application Priority Data

Nov. 30, 2004   (JP)   .............................. 2004-345419

(51) Int. Cl.
*F21V 29/00*   (2006.01)
(52) U.S. Cl. .................. 362/294; 362/202; 362/268
(58) Field of Classification Search ................ 362/171, 362/172, 202, 203, 800, 294; 257/98, 100
See application file for complete search history.

(56) References Cited

U.S. PATENT DOCUMENTS 6,481,874 B2 * 11/2002 Petroski ....................... 362/373
6,517,218 B2 * 2/2003 Hochstein .................... 362/294
6,827,468 B2 * 12/2004 Galli ........................... 362/294

FOREIGN PATENT DOCUMENTS

| JP | 3-99155 | 10/1991 |
| JP | 3099155 | 10/2003 |
| JP | 2004-111377 | 4/2004 |
| JP | 2005-300321 | 10/2005 |

* cited by examiner

*Primary Examiner*—Ali Alavi (57) ABSTRACT

The light irradiation device of this invention intends to further facilitate an assembling procedure and to stabilize the quality as a product.

The light irradiation device comprises an LED 5, an optical unit 4 that makes an engagement with the LED 5 with their axial lines aligned with each other, a tubular first housing element 2 having an opening D at its rear end surface for inserting the optical unit 4 and the LED 5 into the inside of the first housing element 2, a deciduous inhibition member R that makes an engagement with a vicinity of the opening D of the first housing element 2 and that prevents the optical unit 4 that has been inserted into the first housing element 2 from dropping off, a second housing element 3 that blocks up the opening D by being mounted on a predetermined position of the first housing element 2 and that forms a housing CS together with the first housing element 2, and a projecting member 10 that is arranged on the second housing element 3 to project forward, and at the predetermined position, the projecting member 10 presses the rear surface of the LED 5 to engage the optical unit 4 and the LED 5, thereby to align their axial lines.

20 Claims, 7 Drawing Sheets

LIGHT IRRADIATION DEVICE

FIELD OF THE ART

This invention relates to a light irradiation device used for inspection of appearance, flaw or finish of a product by irradiating light in a factory or the like.

BACKGROUND ART

Recently, as this kind of a light irradiation device for production inspection, an LED of a super high-intensity type referred to as a power LED is used as a light source. With this power LED, it is possible to obtain sufficient illumination intensity with a single power LED without using multiple LEDs and to simplify optical systems compared with a case of using multiple LEDs, thereby to simplify a structure of the light irradiation device.

As the light irradiation device using the power LED, the applicant of the present claimed invention has invented the light irradiation device shown in the patent document 1.

The light irradiation device has an arrangement wherein a housing can be separated into a rear side housing element of a cupped shape and a front side housing element, the rear side housing element and the front side housing element are threadably connected each other with their axial lines aligned with each other, an LED and an optical system accommodated inside of the housing elements are pressed between the front and the back through an elastic member such as an O-ring with an axial line of the LED aligned with an axial line of the optical system in a process of coupling the rear and front side housing elements. Then the light irradiation device is innovative because it can be assembled with high accuracy of position easily and heat also can be effectively dissipated with an arrangement wherein the housing is tightly attached to the LED.

Patent document 1: Japan patent laid-open number 2004-111377

DISCLOSURE OF THE INVENTION

Problems to be Solved by the Invention

For the above-mentioned light irradiation device, in order to place the LED and the optical system into one housing element, a thermal conduction member is placed between the housing and the rear face of the LED for thermal conduction and then the LED and the optical system are inserted to be stacked in this order. And finally other housing element is connected, however, since both areas of the thermal conduction member, the LED are small and they are placed prior to the optical unit, it is difficult to align them and to find displacement that might happen, then the light irradiation device might be productized without verifying the displacement.

In addition, since the housing elements are connected each other by rotating the housing elements, the LED is previously accommodated in the housing element on which a connector for power supply is to be mounted. If the LED is accommodated in the other housing element, several problems such as breaking of wire might be generated because the cable between the connector and the LED might be twisted in the process of connecting the housing elements. From a view point of a wiring operation, this arrangement wherein the connector and the LED are held by a single housing element is not very preferable.

In addition, since the housing elements are threadably connected, if extremely spoken, the housing elements might approach each other too much when the housing element is rotated too much and shear force generates due to the rotational movement and then the O-ring might be broken due to overload applied to the O-ring. Contrary, when the housing elements are not connected securely due to lack of the rotational movement, there is a problem that quality control is difficult in case of mass production.

Furthermore, even though each of a size of the optical unit, a size of the LED (especially a height) and a machining accuracy of each component is within an error range, the error might have an effect on an actual manufacturing process. Then for the light irradiation device wherein the LED and the optical unit are stacked, an accumulated error for each component generates (gets bigger), and the suppressing force varies for each light irradiation device. As a result, there is a problem that there might be a case the light irradiation device of a stable quality is difficult to be provided due to the fluctuation of the suppressing force for every light irradiation device.

Then the present claimed invention intends to solve all of the above-mentioned problems and a main object is to further facilitate a procedure relating to assembling the light irradiation device and to stabilize the quality of the light irradiation device as a product, for the light irradiation device having an arrangement wherein the LED and the optical system accommodated inside of a first housing element can be positioned at the same time when a first housing element are connected with a second housing element so as to form a housing.

Means to Solve the Problems

More specifically, the light irradiation device in accordance with this invention comprises an LED that irradiates light forward, an optical unit that makes an engagement with the LED with their axial lines aligned with each other by approaching the LED from the front side of the LED, a tubular first housing element having an opening at its rear end surface for inserting the optical unit, the LED and a thermal conduction member to be tightly attached to a rear surface of the LED into the inside of the first housing element in this order, a deciduous inhibition member that makes an engagement with a vicinity of the opening of the first housing element and that prevents the optical unit, the LED and the thermal conduction member that have been inserted into the first housing element from dropping off, a second housing element that blocks up the opening by being mounted on a predetermined position of the first housing element and that forms a housing together with the first housing element, and a projecting member that is arranged on the second housing element to project forward, wherein, at the predetermined position, the projecting member presses the rear surface of the LED through the thermal conduction member to engage the optical unit and the LED, thereby to align their axial lines.

In accordance with this arrangement, since the LED and the thermal conduction member as being small components are inserted into the first housing element after the optical unit is inserted into the first housing element, an assembling procedure can be simplified and the assembling procedure can be conducted with confirming that the thermal conduction member is set accurately to the LED until just before connecting the first and the second housing elements.

In addition, since the light irradiation device is provided with the deciduous inhibition member, there is no chance for the optical system component to unexpectedly drop while connecting the first housing member and the second housing member, and also in this point the assembling procedure can be facilitated.

Furthermore, since the second housing element is mounted on the predetermined position of the first housing element and a relative positional relationship between them is not affected by a personnel who assembles the light irradiation device but becomes uniform, it is possible to provide the light irradiation device of a stable quality without any difference in a transformation degree of the O-ring for each light irradiation device.

As one embodiment to prevent misalignment of the LED in the radial direction, the optical unit may be inserted into the first housing element without allowing almost any bumpy movement in a radial direction. With this arrangement, the LED makes an engagement with the optical unit and consequently the position of the LED in the radial direction is decided. In addition, with this arrangement, it is preferable that the thermal conduction member is held by an annular supporting member that is inserted into the first housing element without allowing almost any bumpy movement in the radial direction, and the thermal conduction member is inserted into the first housing element together with the supporting member. In accordance with this arrangement, since the thermal conduction member also will not be misaligned in the radial direction, the thermal conduction member makes a contact with the rear surface of the LED steadily.

In order to facilitate a wiring procedure in assembling or conducting maintenance, it is preferable that the second housing element is fitted with the first housing element with a sliding movement along a direction of the axial line and a connector for supplying power to the LED is mounted on the second housing element.

More concretely, it is represented that the second housing element comprises a tubular side peripheral wall that makes a sliding movement to fit over the first housing element and a bottom wall that blocks up a rear end surface of the side peripheral wall, and a cable communicating path that penetrates the bottom wall is arranged, a connector is mounted on the cable communicating path so as to block up a rear end opening of the cable communicating path, and the connector and the LED are connected by a cable that is inserted into and passes through the cable communicating path.

In order to set a position where the second housing element is mounted on the first housing element at the predetermined position certainly with a simple arrangement, it is preferable that the second housing element comprises a small diameter chamber into which the first housing element is inserted without allowing any bumpy movement with a sliding movement and a big diameter chamber that is arranged continuously to the small diameter chamber in the axial line direction, and the first housing element has a collar part at an end position locating at a side opposite to a sliding direction for insertion and the collar part is arranged to inhibit a further sliding movement by interfering with a step part between the big diameter chamber and the small diameter chamber of the second housing element at the predetermined position.

As a concrete embodiment of the present claimed invention preferable for spotlighting with big illumination, it is represented that the second housing element holds a lens at its front end portion by extending forward in front of the first housing element.

As a concrete embodiment wherein an effect of this invention becomes especially remarkable, it is represented that the LED is a power LED that can continuously pass current of not less than 200 mA.

The LED described in this specification is a PN junction semiconductor, and so-called a LED package composed of an LED element as being a component that actually emits light, a base on which the LED element is loaded, a molded component that covers the LED element and a lead wire to be connected to a printed substrate.

EFFECT OF THE INVENTION

In accordance with the present claimed invention, the assembling procedure can be further facilitated and the quality can be stabilized for the light irradiation device having an arrangement wherein the LED and the optical system accommodated inside of the first housing element can be positioned at the same time when the first housing element and the second housing element are connected.

EXPLANATION OF THE CODE 1. light irradiation unit, 2. first housing element, 3. second housing element, 31. side peripheral wall, 32. bottom wall, 3a. small diameter chamber, 3b. big diameter chamber, 32a. cable communicating path, 4. optical unit, 5. LED, 7. supporting member, 8. lens, 10. projecting member, S. thermal conduction member (spacer), D. opening, R. deciduous inhibition member (snap ring), CS. housing, CN. connector, CA. cable

BEST MODES OF EMBODYING THE INVENTION

An embodiment of the present claimed invention will be explained with reference to drawings.

A light irradiating device 1 in accordance with this embodiment comprises, as shown in FIG. 1 through FIG. 4, a single LED that irradiates light forward, an optical unit 4 that makes an engagement with the LED 5 with their axial lines aligned with each other by approaching the LED 5 from the front side with a sliding movement, a columnar light guide 9 that is arranged in front of the optical unit 4, a lens 8 that is arranged in front of the light guide 9, and a housing CS that holds the LED 5, the optical unit 4, the light guide 9 and the lens 8.

In the following explanation, for the sake of convenience, a traveling direction of the light is defined as a front direction and its opposite direction is defined as a back direction, however, it goes without saying that this direction may be changed in accordance with an installation posture of the light irradiating device 1.

Figure 6:
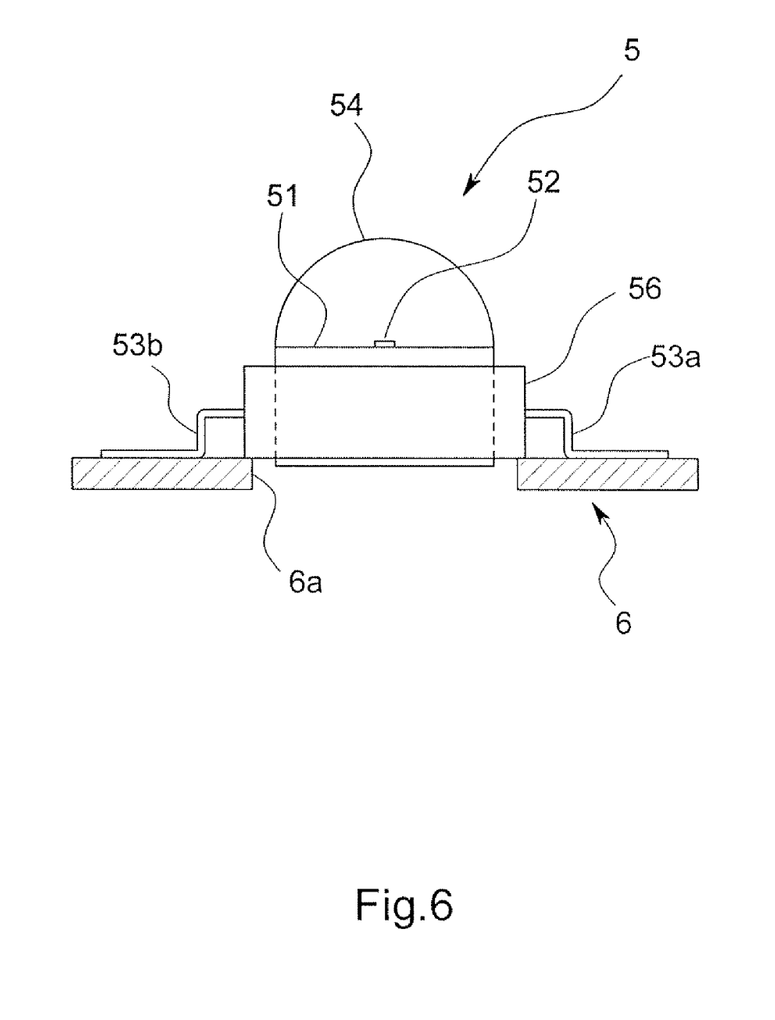
FIG. 6 is a side view showing an LED and a substrate in accordance with the embodiment.

Each component will be explained. As details are shown in FIG. 6, the LED 5 is a packaged component comprising a base 51 as being a high thermal conductance body made of metal (for example, made of copper), an LED element 52 fixed on the base 51 by means of die bonding or the like, a resin frame 56 that supports the base 51 by fittingly inserting over the base 51, two lead wires 53a, 53b each of which is connected to an electrode in a cathode side and an electrode in an anode side of the LED element 52 respectively, and the resin molded part 54 made of material (plastic such as epoxy or silicon, elastomer or glass or the like) having transparency to tightly seal and protect the LED element 52 or the like. The LED 5 is so-called a power LED that can pass current of not less than 200~300 mA continuously.

Then the LED 5 is mounted on a toric printed substrate 6 having a center opening 6a with a back surface of the base 51 exposed from the center opening 6a.

Figure 7:
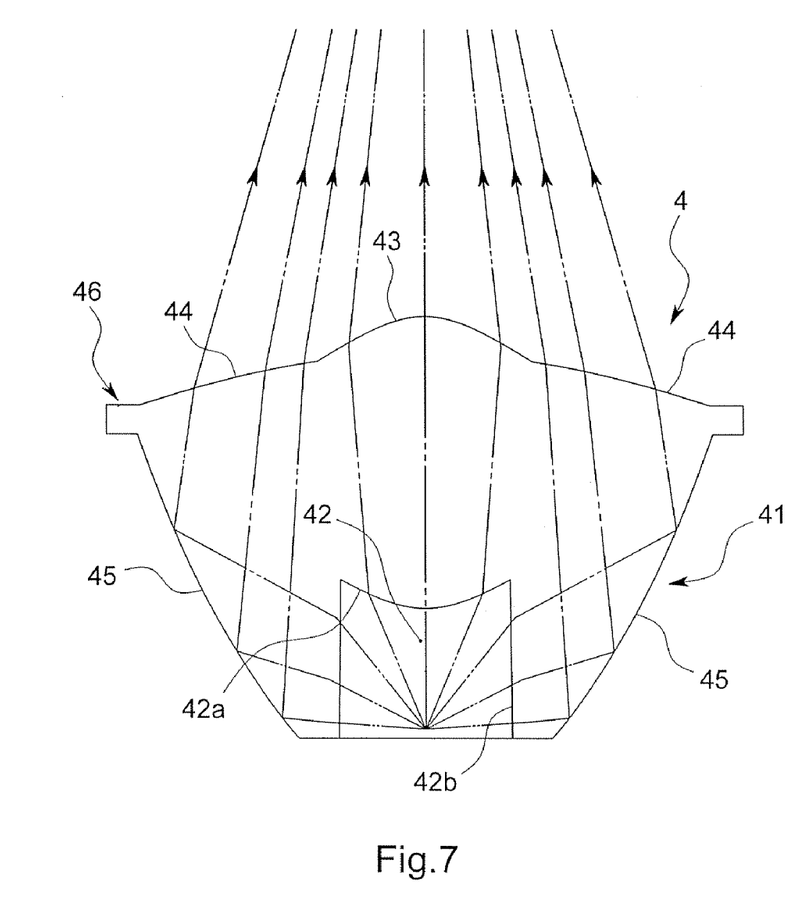
FIG. 7 is a side view showing an optical unit in accordance with the embodiment.

As details are shown in FIG. 7, the optical unit 4 is made of transparent resin integrally formed with a solid transparent body 41 in a shape of a body of revolution whose cross-sectional area gradually increases from a proximal end to a distal end and a collar part 46 arranged at an outer circumferential edge of a distal end portion of the body 41.

A concave part 42 is arranged to open at a proximal end surface of the body 41. The concave part 42 is inserted over an outer circumference of the resin molded part 54 without allowing any bumpy movement with the axial line of the optical unit 4 aligned with the axial line of the LED 5. A bottom surface 42a of the concave part 42 is formed to be in a shape of a convex lens expanding toward a distal end side. A center convex lens part 43 is formed at a distal end surface of the body 41 by expanding its center part and a ring-shaped convex lens part 44 whose curvature differs from that of the center convex lens part 43 is formed to surround the center convex lens part 43. Furthermore, a curved expanding surface 45 as being a reflecting element is arranged on a side surface of the body 41 with its cross-sectional outline forming a parabola.

As shown in FIG. 7 (the LED is omitted to show in this drawing), it is so arranged that generally all light passing a side surface 42b of the concave part 42 among the light irradiated from the LED 5 reaches the curved expanding surface 45 and is totally reflected by the curved expanding surface 45 and then the reflected light is emitted outside as the light approaching each other toward the axial line through the ring-shaped convex lens part 44. It is so arranged that generally all light passing the bottom surface 42a of the concave part 42 by refraction among the light irradiated from the LED 5 is also emitted outside as the light approaching each other toward the axial line through the center convex lens part 43. A focusing position of the light from the center convex lens part 43 is set to be generally the same as a focusing position of the light from the ring-shaped convex lens part 44.

Figure 5:
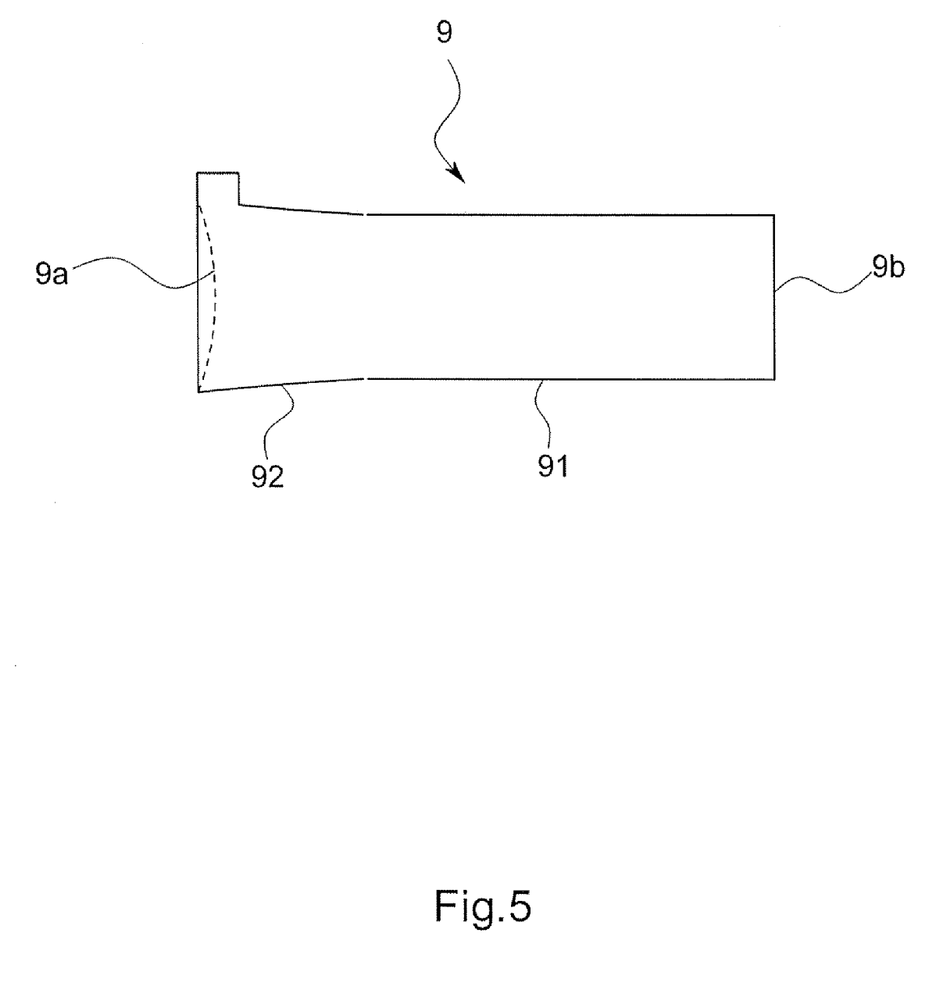
FIG. 5 is a side view showing a light guide of the light irradiation device in accordance with the embodiment.

As shown in FIG. 5, the columnar light guide 9 that can also be called as a second optical unit has a cylindrical column part 91 with a uniform diameter arranged at a distal end side (front side) and a diameter expanding part 92 of a partial circular cone shape that gradually expands its diameter from a proximal end of the cylindrical column part 91, and an end surface 9a of the diameter expanding part 92 is curved in a concave shape. The light guide 9 is arranged both to align its axial line with the axial line of the optical unit 4 and to generally coincide the end surface 9a with the focusing position of the light passing from the optical unit 4. Then generally all of the light passing from the optical unit 4 is introduced into the inside of the light guide 9 from the proximal end surface 9a. Some of the light introduced into the inside of the light guide 9 goes straight and some of the light totally reflects inward against a side circumferential surface and then the mixed light is emitted forward from all area of the distal end surface 9b as the even light. In addition, since a center portion of the end surface 9a (light introducing surface 9a) is provided with a diffusion processing, it is possible to effectively diffuse only the light that has passed the refraction element 42a, 43 of the optical unit 4 and that has imaging characteristics, thereby to minimize loss of the light intensity and to further decrease unevenness of the light intensity.

Figure 1:
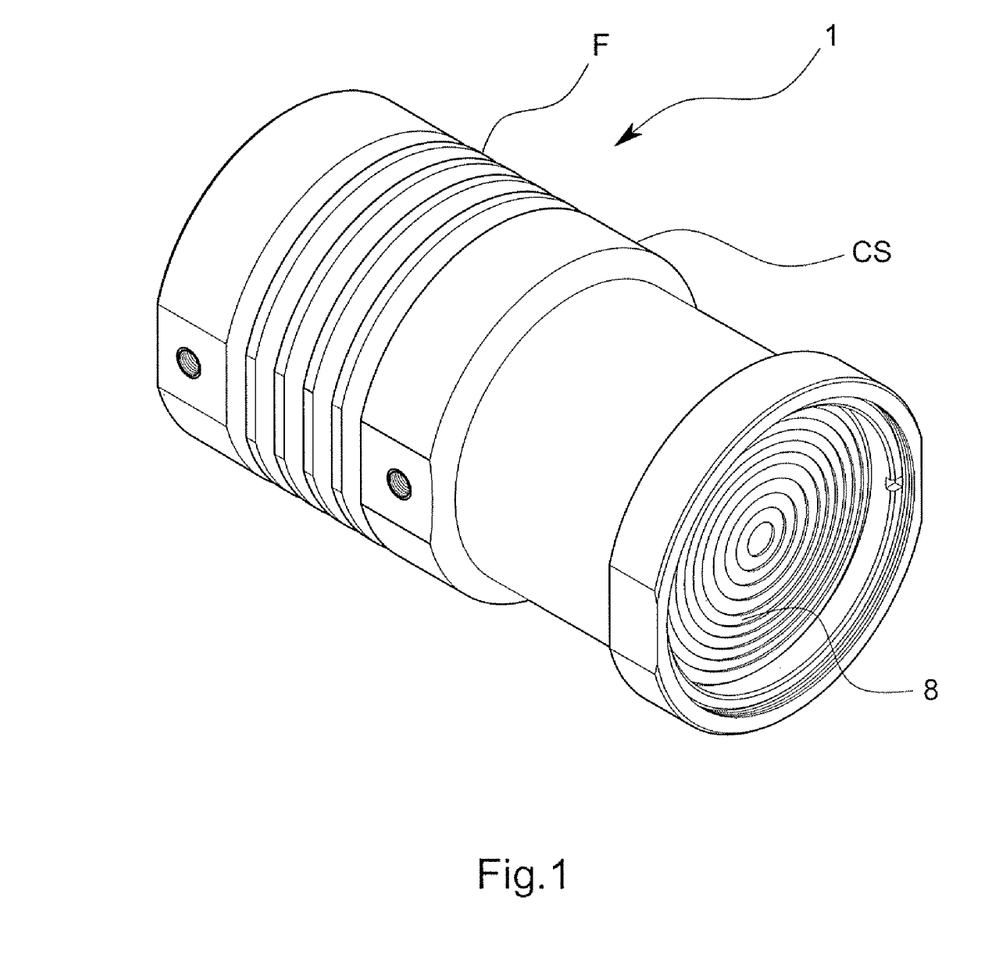
FIG. 1 is an overall perspective view showing a light irradiation device in accordance with an embodiment of the present claimed invention.
Figure 2:
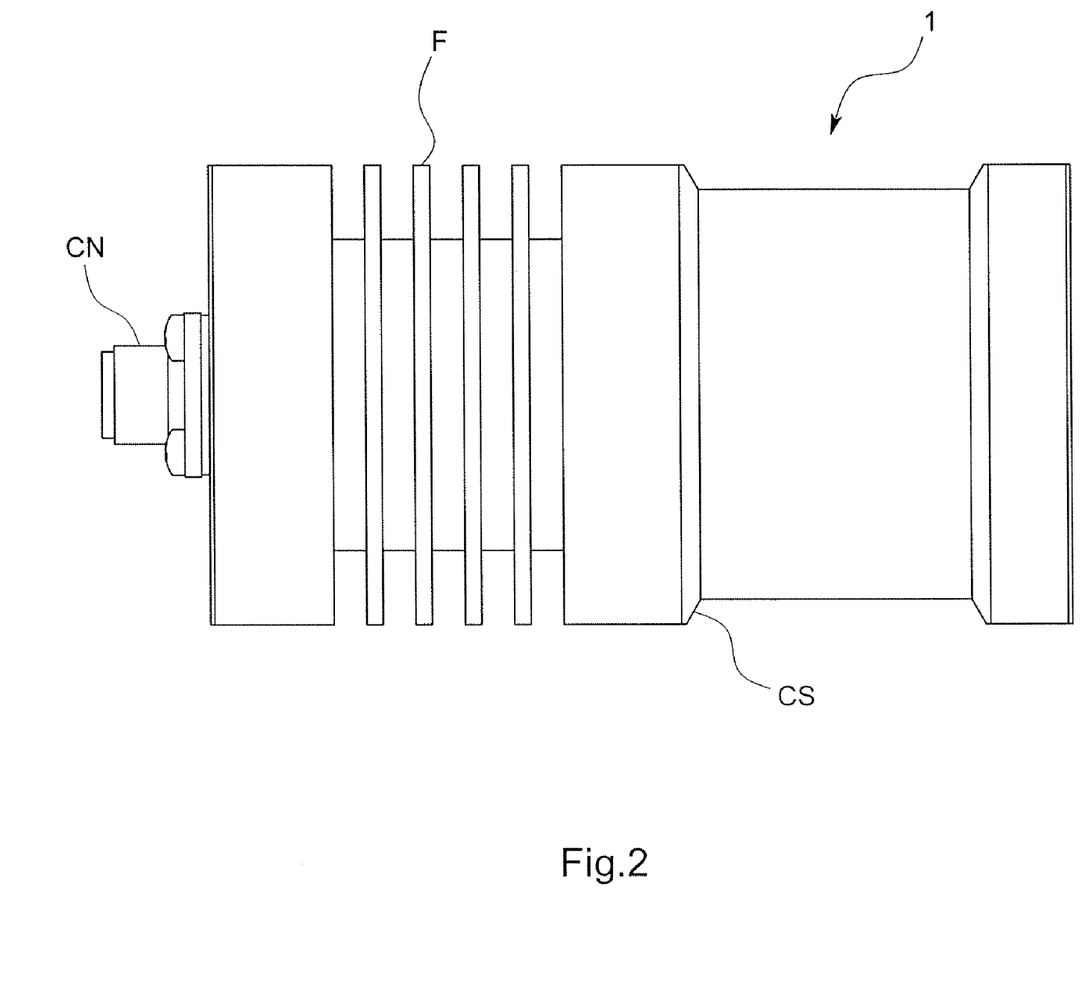
FIG. 2 is a side view showing the light irradiation device in accordance with the embodiment.
Figure 3:
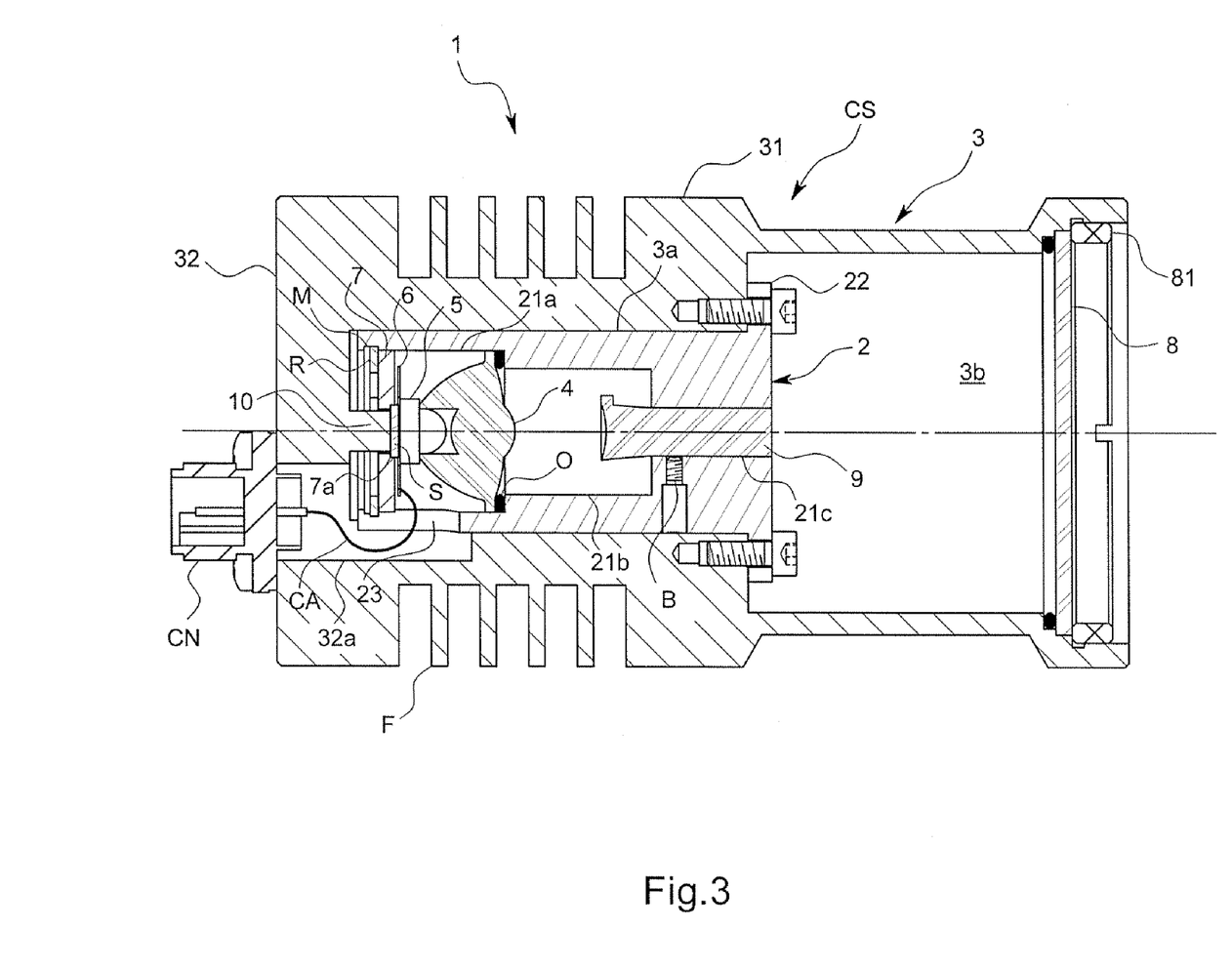
FIG. 3 is a longitudinal sectional view showing an internal structure of the light irradiation device in accordance with the embodiment.

The lens 8 that can also be called as a third optical unit is a condenser lens and may be a convex lens, and as shown in FIG. 3, in this embodiment a Fresnel lens is used as the lens 8 for downsizing and weight saving. The Fresnel lens 8 also is arranged with its axial line aligned with the axial line C and emits the light outside as the spot light with refracting the light irradiated from the light guide 9 inward (direction of the axial line).

The LED 5 and the optical system components 4, 8, 9 are integrally formed with supported by the housing CS.

As shown in FIG. 3, the housing CS is formed by connecting the first housing element 2 of a general cylinder shape and the second housing element 3 fittingly inserted over the first housing element 2 without allowing bumpy movement.

Figure 4:
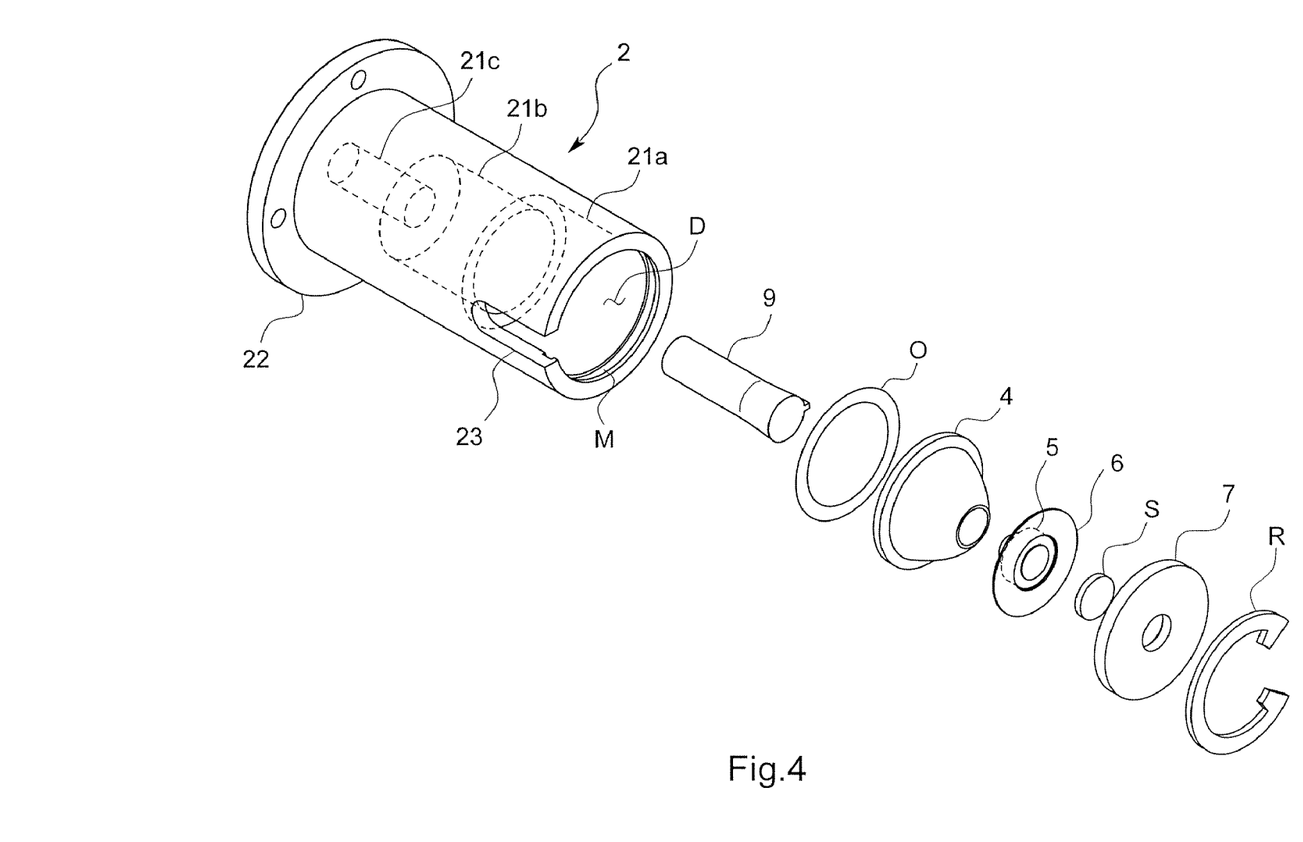
FIG. 4 is an exploded perspective view of the light irradiation device in accordance with the embodiment.

As shown in FIG. 3 and FIG. 4, the first housing element 2 has a through bore penetrating the center of the first housing element 2 in the axial line, and the through bore comprises a big diameter part 21a formed at the proximal end portion (rear end portion), a middle diameter part 21b formed with a step from a distal end of the big diameter part 21a, and a small diameter part 21c formed with a step from a distal end of the middle diameter part 21b.

The big diameter part 21a is a space to accommodate the optical unit 4, the LED 5 or the like and its internal diameter is set to be generally the same as an outer diameter of the collar part 46 of the optical unit 4 so that the optical unit 4 can be inserted thereinto without allowing almost any bumpy movement in the radial direction. A groove M is arranged at a distal end portion of the internal peripheral surface of the big diameter part 21a, and the optical unit 4 and the LED 5 are inserted from a distal end (rear end) opening D in this order and a snap ring R (C-ring or E-ring) as being a deciduous inhibition member is inserted into the groove M so that the optical unit 4 and the LED 5 are held by the big diameter part 21 in a manner incapable of being pulled out with a little allowance to move in the axial direction.

As components accommodated in the big diameter part 21 and held by the snap ring R, there are an O-ring O lying between a front surface of the collar part 41a of the optical unit 4 and a rear facing surface of the big diameter part 21a, an insulating spacer S made of a high thermal conduction material such as aluminum nitride that tightly attaches to the rear surface of the LED 5, and a toric supporting member 7 having a concave sunken part 7a at a center thereof into which the insulating spacer S is inserted without allowing bumpy movement. The supporting member 7 is inserted into the big diameter part 21a without allowing bumpy movement in the radial direction. In addition, a cut-out 23 is formed on the side peripheral wall that forms the big diameter part 21a in order to pass a cable CA to be connected to the LED 5.

A diameter of the small diameter part 21c is generally the same as that of the cylindrical column part 91 of the light guide 9 and the small diameter part 21c accommodates the cylindrical column part 91 without allowing bumpy movement in the radial direction through a thin air layer. The cylindrical column part 91 is fixed by a setscrew B inserted from the radial direction. The tapered part 92 locates in the middle diameter part 21b to project rearward from the small diameter part 21c.

The second housing element 3 comprises, as shown in FIG. 3, a side peripheral wall 31 where multiple fins F for heat dissipation are formed and a bottom wall 32 that blocks up the rear end surface of the side peripheral wall 31, and an internal space surrounded by the side peripheral wall 31 and the bottom wall 32 comprises a small diameter chamber 3a set at a proximal end side (rear side) and a big diameter chamber 3b continuously formed in front of the small diameter chamber 3a with their axial lines aligned with each other.

An internal diameter of the small diameter chamber 3a is generally the same as the external diameter of the first housing element 2, and the first housing element 2 is held by the small diameter chamber 3a without allowing bumpy movement by fittingly inserting in the axial line with a sliding movement into the small diameter chamber 3a from the front direction. A collar part 22 is arranged at the distal end portion of the first housing element 2 and when the first housing element 2 is inserted into the small diameter chamber 3a, the collar part 22 makes a contact with a step part between the small diameter chamber 3a and the big diameter chamber 3b at a predetermined position and prevents further insertion so that a depth by which the first housing element 2 is inserted is kept constant. The first housing element 2 is fixed to the step part in a manner incapable of being pulled out with the collar part 22 screwed up in the step part.

A diameter of the big diameter chamber 3b is generally the same as an external diameter of the lens 8 and the lens 8 is fixed to the distal end portion (front end portion) of the big diameter chamber 3b with a ring screw 81.

A cable communicating bore 32a communicating with the small diameter chamber 3a is arranged on the bottom wall 32 of the second housing element 3, and a connector CN for power supply to the LED 5 is mounted so as to block up the rear end surface of the communicating bore 32a. Then the cable CA extending from a rear surface of the connector CN can be connected to the substrate 6 that loads the LED 5.

Furthermore, a columnar projecting member 10 is integrally formed to project toward the small diameter chamber 3a in the axial line from the center of the bottom wall 32 of the second housing element 3.

A length of the projecting member 10 is so set that a distal end surface of the projecting member 10 tightly attaches and presses the rear surface of the LED 5 through the insulating spacer S so as to elastically transform the O-ring O to a certain degree when the first housing element 2 is fittingly inserted into the small diameter chamber 3a to a predetermined position with a sliding movement. This makes the LED 5 firmly fit into the optical unit 4 and fixes each other with their axial lines aligned with each other.

Next, an operation to assemble the light irradiation device 1 having the above arrangement will be explained.

First, the LED 5 and the optical system components are incorporated into the first housing element 2. More specifically, as shown in FIG. 4, the light guide 9, the O-ring O, the optical unit 4, the LED 5 loaded on the substrate 6, the spacer S and the supporting member 7 are inserted in this order into the big diameter part 21a of the first housing member 2 from the rear end opening D. At this time the wiring cable CA (omitted to show in this drawing) is previously connected to the substrate 6 and a distal end of the wiring cable CA is drawn out through the cut-out 23. In addition, the light guide 9 is fixed with the setscrew B.

The snap ring R is fittingly inserted into the proximal end of the big diameter part 21a and is tentatively held so that each component inserted in the first housing element 2 does not fall off from the first housing element 2.

With this state, each component except for the light guide 9 accommodated in the first housing element 2 has a little room to move in the axial line, however, there is no room for each component except for the light guide 9 to move in the radial direction with each axial line aligned with the axial line of the first housing element 2.

More specifically, the optical unit 4 is fittingly inserted into the first housing element 2 without allowing any bumpy movement in the radial direction and the LED 5 also is fittingly inserted into the concave part 42 of the optical unit 4 so that the LED 5 can hardly move in the radial direction. In addition, since the supporting member 7 is fittingly inserted into the first housing element 2 without allowing any bumpy movement in the radial direction, the spacer S fittingly inserted into the concave sunken part 7a also can not move in the radial direction.

Next, the first housing element 2 into which each component is incorporated is fittingly inserted from the front direction into the small diameter chamber 3a of the second housing element 3 with a sliding movement. Then the first housing element 2 is screwed up so that the collar part 22 of the first housing element 2 locates at a position where the collar part 22 makes a contact with the step part of the second housing element 3.

During this process, the projecting member 10 enters inside of the first housing element 2 from the rear end opening D of the first housing element 2, makes a tight contact with the spacer S after passing through the center bore of the supporting member 7 and presses the rear surface of the LED 5 through the spacer S.

As a result, the LED 5 fits into the optical unit 4 without allowing any bumpy movement, and the O-ring O is pressed between the front surface of the collar part 46 of the optical unit 4 and the rear facing surface of the step part between the small diameter part 21c and the middle diameter part 21b so that the LED 5 is transformed in the axial line by a predetermined amount. The optical unit 4 and the LED 5 are pressed between the back and the front by means of the elastic repulsive force of the O-ring O and the suppressing force from the projecting member 10, and the optical unit 4 is fixed to the LED 5 with their axial lines aligned with the axial line of the first housing element 2 by means of fitting each other during its pressing process.

Meanwhile, the connector CN is previously removed from the bottom wall 22, and after the first and second housing elements 2, 3 are connected and the LED 5 is fixed, the removed connector CN is connected to the cable CA extending outside from the cable communicating bore 32a. Then the connector CN is mounted on the bottom wall 22 with inserting the remainder of the cable CA into inside of the housing CS.

Finally, the Fresnel lens 8 is fixed to the front end portion of the second housing element 3 with the ring screw 81.

In accordance with this arrangement, since the LED 5 that is a small component and that requires an accuracy of position and the spacer S are inserted into the first housing element 2 after the optical unit 4 is inserted into the first housing element 2, an assembling procedure can be simplified and the assembling procedure can be conducted with confirming that the spacer S is set accurately to the LED 5 until just before connecting the first and the second housing elements 2, 3. In addition, since the LED 5 and the spacer S can move a little in the direction of the axial line but can not move in the radial direction, there is no chance for the LED 5 and the spacer S to be unexpectedly misaligned while connecting the first housing element 2 and the second housing element 3.

As mentioned above, in the assembling procedure, it is possible to position the spacer S on the rear surface of the LED 5 easily and accurately without misalignment and to thermally connect the LED 5 with the housing CS through the projecting member 10.

In addition, due to the snap ring R as being the deciduous inhibition member there is no chance for the component to unexpectedly drop while connecting the first housing element 2 with the second housing element 3, and also in this point the assembling procedure can be facilitated.

Furthermore, since a positional relationship between the second housing element 3 and the first housing element 2 is not affected by a personnel who assembles the light irradiation device 1 but becomes always constant due to the collar part 22, it is possible to provide the light irradiation device 1 of a stable quality without any difference in a transformation degree of the O-ring O for each light irradiation device 1.

In addition, since the first housing element 2 is connected with the second housing element 3 not threadably but slidingly, there is no need of considering that the cable CA might be twisted, thereby to simplify a process relating to wiring.

Furthermore, although a size of the optical unit 4, a size of the LED 5 loaded on the substrate 6 (especially a height of the resin molded part 54) and a machining accuracy of each component are within an error range, they might have an effect on an actual manufacturing process. With the light irradiation device 1 of the present claimed invention having an arrangement wherein the LED 5 and the optical unit 4 are stacked, since an accumulated error for each component is difficult to be produced (difficult to get bigger), there is no danger of changing the suppressing force for each light irradiation device 1. As a result, there is no fluctuation of the suppressing force for every light irradiation device 1, thereby to provide the light irradiation device 1 of a stable quality.

This invention is not limited to the above-mentioned embodiment. A shape of the housing, a shape and a function of the LED or the optical unit may be variously modified, and it goes without saying that the optical system such as the light guide or the Fresnel lens is not limited to the above-mentioned embodiment.

POSSIBLE APPLICATIONS IN INDUSTRY

As mentioned above, the light irradiation device in accordance with the present claimed invention is preferably used both to further facilitate the assembling procedure and to stabilize the quality for the light irradiation device having an arrangement wherein the LED and the optical system accommodated inside of the first housing element can be positioned at the same time when the first housing element and the second housing element are connected.

The invention claimed is:

1. A light irradiation device comprising
   an LED that irradiates light forward,
   an optical unit that makes an engagement with the LED with their axial lines aligned with each other by approaching the LED from the front side of the LED,
   a tubular first housing element having an opening at its rear end surface for inserting the optical unit, the LED and a thermal conduction member to be tightly attached to a rear surface of the LED into the inside of the first housing element in this order,
   a deciduous inhibition member that makes an engagement with a vicinity of the opening of the first housing element and that prevents the optical unit, the LED and the thermal conduction member that have been inserted into the first housing element from dropping off,
   a second housing element that blocks up the opening by being mounted on a predetermined position of the first housing element and that forms a housing together with the first housing element, and
   a projecting member that is arranged on the second housing element to project forward,
   wherein, at the predetermined position, the projecting member presses the rear surface of the LED through the thermal conduction member to engage the optical unit and the LED, thereby to align their axial lines.

2. The light irradiation device described in claim 1, wherein
   the optical unit is inserted into the first housing element without allowing almost any bumpy movement in a radial direction, and
   the thermal conduction member is held by an annular supporting member that is inserted into the first housing element without allowing almost any bumpy movement in the radial direction, and inserted into the first housing element together with the supporting member.

3. The light irradiation device described in claim 1, wherein
   the second housing element is fitted with the first housing element with a sliding movement along a direction of the axial line and a connector for supplying power to the LED is mounted on the second housing element.

4. The light irradiation device described in claim 1, wherein
   the second housing element comprises a tubular side peripheral wall that makes a sliding movement to fit over the first housing element and a bottom wall that blocks up a rear end surface of the side peripheral wall, wherein
   a cable communicating path that penetrates the bottom wall is arranged, a connector is mounted on the cable communicating path so as to block up a rear end opening of the cable communicating path, and the connector and the LED are connected by a cable that is inserted into and passes through the cable communicating path.

5. The light irradiation device described in claim 1, wherein
   the second housing element comprises a small diameter chamber into which the first housing element is inserted with a sliding movement without allowing any bumpy movement and a big diameter chamber that is arranged continuously to the small diameter chamber in the axial line direction, wherein
   the first housing element has a collar part at an end position locating at a side opposite to a sliding direction for insertion and the collar part is arranged to inhibit a further sliding movement by interfering with a step part between the big diameter chamber and the small diameter chamber of the second housing element at the predetermined position.

6. The light irradiation device described in claim 1, wherein
   the second housing element holds a lens at its front end portion by extending forward in front of the first housing element.

7. The light irradiation device described in claim 1, wherein
   the LED is a power LED that can continuously pass current of not less than 200 mA.

8. The light irradiation device described in claim 2, wherein
   the second housing element is fitted with the first housing element with a sliding movement along a direction of the axial line and a connector for supplying power to the LED is mounted on the second housing element.

9. The light irradiation device described in claim 2, wherein the second housing element comprises a tubular side peripheral wall that makes a sliding movement to fit over the first housing element and a bottom wall that blocks up a rear end surface of the side peripheral wall, wherein
a cable communicating path that penetrates the bottom wall is arranged, a connector is mounted on the cable communicating path so as to block up a rear end opening of the cable communicating path, and the connector and the LED are connected by a cable that is inserted into and passes through the cable communicating path.

10. The light irradiation device described in claim 3, wherein the second housing element comprises a tubular side peripheral wall that makes a sliding movement to fit over the first housing element and a bottom wall that blocks up a rear end surface of the side peripheral wall, wherein
a cable communicating path that penetrates the bottom wall is arranged, a connector is mounted on the cable communicating path so as to block up a rear end opening of the cable communicating path, and the connector and the LED are connected by a cable that is inserted into and passes through the cable communicating path.

11. The light irradiation device described in claim 2, wherein
the second housing element comprises a small diameter chamber into which the first housing element is inserted with a sliding movement without allowing any bumpy movement and a big diameter chamber that is arranged continuously to the small diameter chamber in the axial line direction, wherein
the first housing element has a collar part at an end position locating at a side opposite to a sliding direction for insertion and the collar part is arranged to inhibit a further sliding movement by interfering with a step part between the big diameter chamber and the small diameter chamber of the second housing element at the predetermined position.

12. The light irradiation device described in claim 3, wherein
the second housing element comprises a small diameter chamber into which the first housing element is inserted with a sliding movement without allowing any bumpy movement and a big diameter chamber that is arranged continuously to the small diameter chamber in the axial line direction, wherein
the first housing element has a collar part at an end position locating at a side opposite to a sliding direction for insertion and the collar part is arranged to inhibit a further sliding movement by interfering with a step part between the big diameter chamber and the small diameter chamber of the second housing element at the predetermined position.

13. The light irradiation device described in claim 4, wherein
the second housing element comprises a small diameter chamber into which the first housing element is inserted with a sliding movement without allowing any bumpy movement and a big diameter chamber that is arranged continuously to the small diameter chamber in the axial line direction, wherein
the first housing element has a collar part at an end position locating at a side opposite to a sliding direction for insertion and the collar part is arranged to inhibit a further sliding movement by interfering with a step part between the big diameter chamber and the small diameter chamber of the second housing element at the predetermined position.

14. The light irradiation device described in claim 2, wherein
the second housing element holds a lens at its front end portion by extending forward in front of the first housing element.

15. The light irradiation device described in claim 3, wherein
the second housing element holds a lens at its front end portion by extending forward in front of the first housing element.

16. The light irradiation device described in claim 4 wherein
the second housing element holds a lens at its front end portion by extending forward in front of the first housing element.

17. The light irradiation device described in claim 5, wherein
the second housing element holds a lens at its front end portion by extending forward in front of the first housing element.

18. The light irradiation device described in claim 2, wherein
the LED is a power LED that can continuously pass current of not less than 200 mA.

19. The light irradiation device described in claim 3, wherein
the LED is a power LED that can continuously pass current of not less than 200 mA.

20. A light irradiation assembly comprising;
a light emitting diode (LED) having a front light emitting portion and a rear portion;
a first housing member mounting the LED to project light;
an optical unit mounted in the first housing unit to align with and contact the LED, the optical unit condenses the light from the LED about an optical axis;
a light guide member mounted in the first housing unit and aligned with the optical axis of the optical unit to receive and transmit the light from the optical unit; and
a hollow second housing member encompasses and supports the first housing member and includes a projecting member that is aligned with and supports the rear portion of the LED at one end of the second housing member and a lens member at another end of the second housing member that is aligned with the optical axis to transmit the light from the light guide member.

* * * * *